United States Patent
Nevala et al.

(10) Patent No.: US 10,292,618 B2
(45) Date of Patent: May 21, 2019

(54) MR-COIL HOUSING WITH SPACER SHAPED TO MAINTAIN AN ANATOMY RECEIVING SPACE FROM THE MRI BORE WALL

(71) Applicant: KONINKLIJKE PHILIPS N.V., Eindhoven (NL)

(72) Inventors: Mikko Nevala, Eindhoven (NL); Thomas Minahan, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 307 days.

(21) Appl. No.: 15/102,286

(22) PCT Filed: Nov. 28, 2014

(86) PCT No.: PCT/IB2014/066418
§ 371 (c)(1),
(2) Date: Jun. 7, 2016

(87) PCT Pub. No.: WO2015/087190
PCT Pub. Date: Jun. 18, 2015

(65) Prior Publication Data
US 2016/0317064 A1 Nov. 3, 2016

Related U.S. Application Data

(60) Provisional application No. 61/914,111, filed on Dec. 10, 2013.

(51) Int. Cl.
| *A61B 5/05* | (2006.01) |
| *A61B 5/055* | (2006.01) |
| *G01R 33/34* | (2006.01) |

(52) U.S. Cl.
CPC ...... *A61B 5/0555* (2013.01); *G01R 33/34007* (2013.01)

(58) Field of Classification Search
CPC .................. A61B 5/0555; G01R 33/34007
USPC .................................................. 600/407–430
See application file for complete search history.

(56) References Cited

U.S. PATENT DOCUMENTS

| 5,197,474 | A | 3/1993 | Englund | |
| 7,218,106 | B2 | 5/2007 | Yasuhara et al. | |
| 9,770,209 | B2* | 9/2017 | Piron | A61B 5/708 |
| 2006/0106302 | A1 | 5/2006 | Takamori | |
| 2007/0016003 | A1* | 1/2007 | Piron | A61B 5/415 |
| | | | | 600/415 |
| 2008/0306377 | A1* | 12/2008 | Piron | A61B 8/0825 |
| | | | | 600/422 |

(Continued)

FOREIGN PATENT DOCUMENTS

| JP | 63189141 A | 8/1988 |
| JP | 05130980 A | 5/1993 |

(Continued)

*Primary Examiner* — Sanjay Cattungal (57) ABSTRACT

A coil housing for a magnetic resonance ("MR") imaging apparatus, comprises an anatomy receiving space defined by the coil housing, shaped and sized to receive at least a portion of a patient's anatomy to be imaged and a spacer shaped to maintain the anatomy receiving space a first distance from a bore wall of the MR imaging apparatus, the first distance defining an imaging area of the MR imaging apparatus.

17 Claims, 5 Drawing Sheets

(56) References Cited

U.S. PATENT DOCUMENTS

| | | | | |
|---|---|---|---|---|
| 2009/0149738 A1* | 6/2009 | Piron | ............... | G01R 33/34084 600/422 |
| 2009/0216110 A1* | 8/2009 | Piron | ..................... | G01R 33/36 600/415 |
| 2010/0315085 A1* | 12/2010 | Brown | .................. | A61B 5/0555 324/309 |
| 2013/0060129 A1 | 3/2013 | Lee et al. | | |

FOREIGN PATENT DOCUMENTS

| | | |
|---|---|---|
| JP | 2003116808 A | 4/2003 |
| JP | 2013165918 A | 8/2013 |

\* cited by examiner

MR-COIL HOUSING WITH SPACER SHAPED TO MAINTAIN AN ANATOMY RECEIVING SPACE FROM THE MRI BORE WALL

CROSS REFERENCE TO RELATED APPLICATIONS

This application is a U.S. national phase application of International Application No. PCT/IB2014/066418, filed on Nov. 28, 2014, which claims the benefit of U.S. provisional Application Ser. No. 61/914111 filed on Dec. 13, 2013 and is incorporated herein by reference.

FIELD

The exemplary embodiments relate generally to a magnetic resonance (MR) coil housing. Specifically, the exemplary embodiments relates to a MR-coil housing ensuring that a portion of anatomy to be imaged is maintained within a usable imaging area of an MRI device while maintaining internal components of the housing including MR coils a desired distance from a main magnet of the MRI device.

BACKGROUND

Magnetic resonance imaging (MRI) is a medical imaging technique used to diagnose many types of injuries and conditions. An MRI system typically includes a main magnet generating a main magnetic field within an examination region. The magnet is typically arranged so that it surrounds a patient positioned on a patient table. An imaging area of a MRI apparatus is typically limited because the magnet size cannot be easily increased without reducing image quality and the imaging area occupies only a portion of the space within the main magnet. For example, a MRI apparatus with a 70 cm diameter magnet can have an imaging area approximately 60 cm in diameter centered within the main magnet, with a homogeneous imaging area only about 45 cm in diameter centered within the imaging area. Larger patients may present difficulties with such systems as it may be difficult for them to be comfortably situated inside the magnet and to position the portion of anatomy to be imaged within the homogeneous imaging area or even within the imaging area. To obtain images, MR-coils are positioned over the anatomy to be imaged. However, these MR-coils further reduce the usable space within the bore of the MRI apparatus.

The coils of MRI systems should preferably be maintained a certain distance from the magnet. This has generally been addressed by using a separate fixture to position the coils on the patient table.

SUMMARY

The exemplary embodiments are directed to a coil housing for a magnetic resonance ("MR") imaging apparatus comprising an anatomy receiving space defined by the coil housing, shaped and sized to receive at least a portion of a patient's anatomy to be imaged and a spacer shaped to maintain the anatomy receiving space a first distance from a bore wall of the MR imaging apparatus, the first distance defining an imaging are of the MR imaging apparatus.

A housing for MR-coils according to one exemplary embodiment ensures that a portion of a patient's anatomy to be imaged, for example, an arm or a leg, is comfortably maintained in the imaging area while ensuring that the components within the housing, such as the electronic components, are positioned a desired distance from the wall of the main magnet.

Figure 1:
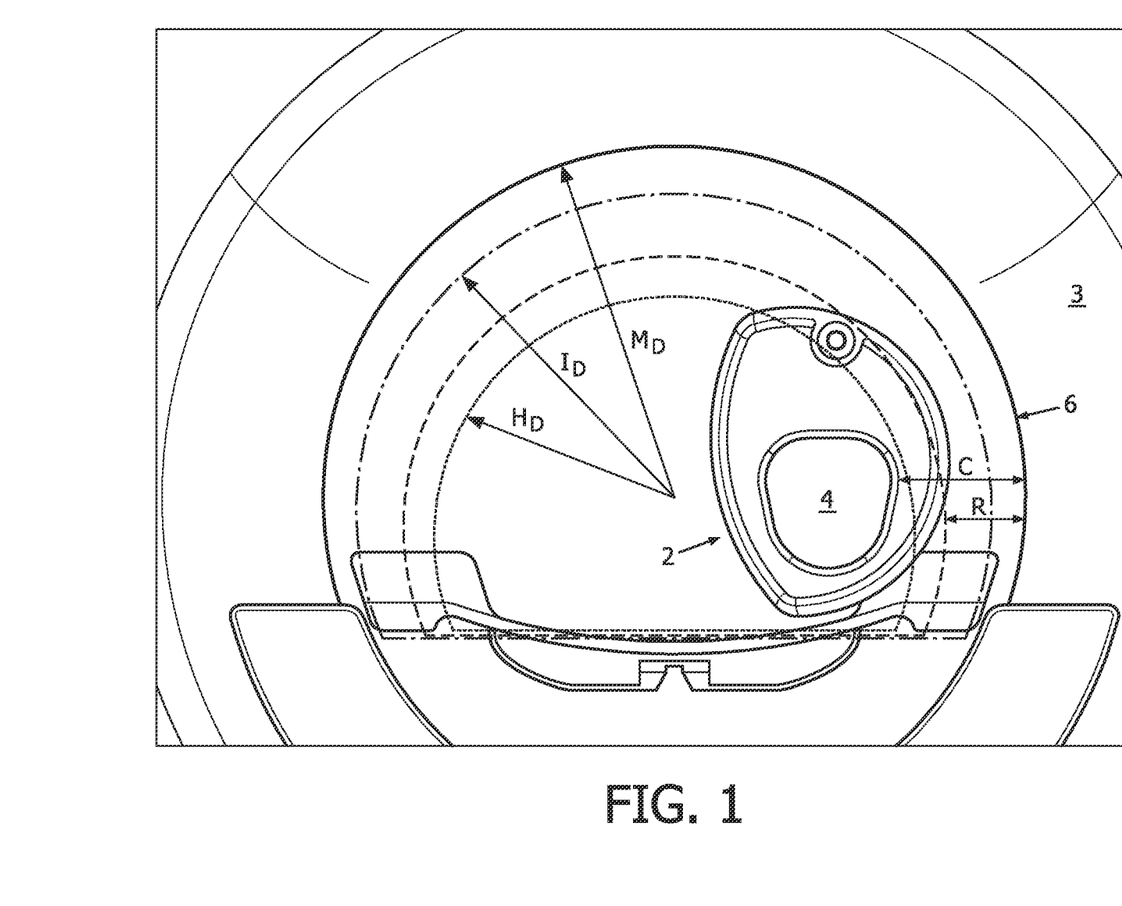
FIG. 1 shows an exemplary embodiment featuring an MRI apparatus with an inner coil housing with a transverse bore in which a portion of a patient's anatomy is to be positioned.

A coil housing according to another exemplary embodiment includes an opening into which the target portion of anatomy is placed and an inner space within which the electronic components such as MR coils are housed. The housing can be shaped so that it cannot be placed within the main magnet in a position which places any part of the target portion of the patient's anatomy outside the imaging area and so that, sensitive components housed in the housing are maintained at least a desired minimum distance from the main magnet. To that end, the housing can be asymmetrical with at least one protrusion (for example a bump, projection, etc.) laterally from a side of the housing. When in an operative position, the protusion can be positioned closest to a wall of the main magnet. Accordingly, the protrusion extends further laterally outward from the anatomy receiving space than does a side which, in the operative position, faces the center of the opening in the main magnet. The anatomy receiving space is formed as a longitudinal lumen substantially similar to those in known MR-coil housings, extending through an entire length of the MR-coil housing to openings at both ends of the housing. The coil housing can be freely placed inside the magnet so long as a radially outer side thereof faces the near wall of the main magnet, because the shape of the radially outer side of the housing is shaped to ensure that target portion of the anatomy always stays in the usable imaging area while maintaining a desired distance between the main magnet and certain components within the coil housing. The housing may be reversed in orientation for placement on the patient's left or right side as those skilled in the art will understand. That is, FIG. 1 shows the coil housing oriented for placement on the right side of a patient. To orient the housing for placement on the left side of the patient, the coil housing is simply rotated 180 degrees so that the side shown in FIG. 1 faces into the MR device.

The exterior of this exemplary coil housing is shaped so that, when pressed against an inner wall of the main magnet housing for support during imaging, space remaining within the main magnet housing for the patient is maximized while ensuring that the target portion of the anatomy and the components within the coil housing are maintained within operable portions of the space within the magnet.

The foregoing summary, as well as the following detailed description of exemplary embodiments, will be better understood when read in conjunction with the appended drawings, which show exemplary embodiments for the purposes of illustration. It should be understood, however, that the application is not limited to the precise arrangements and instrumentalities shown.

DETAILED DESCRIPTION

Figure 2:
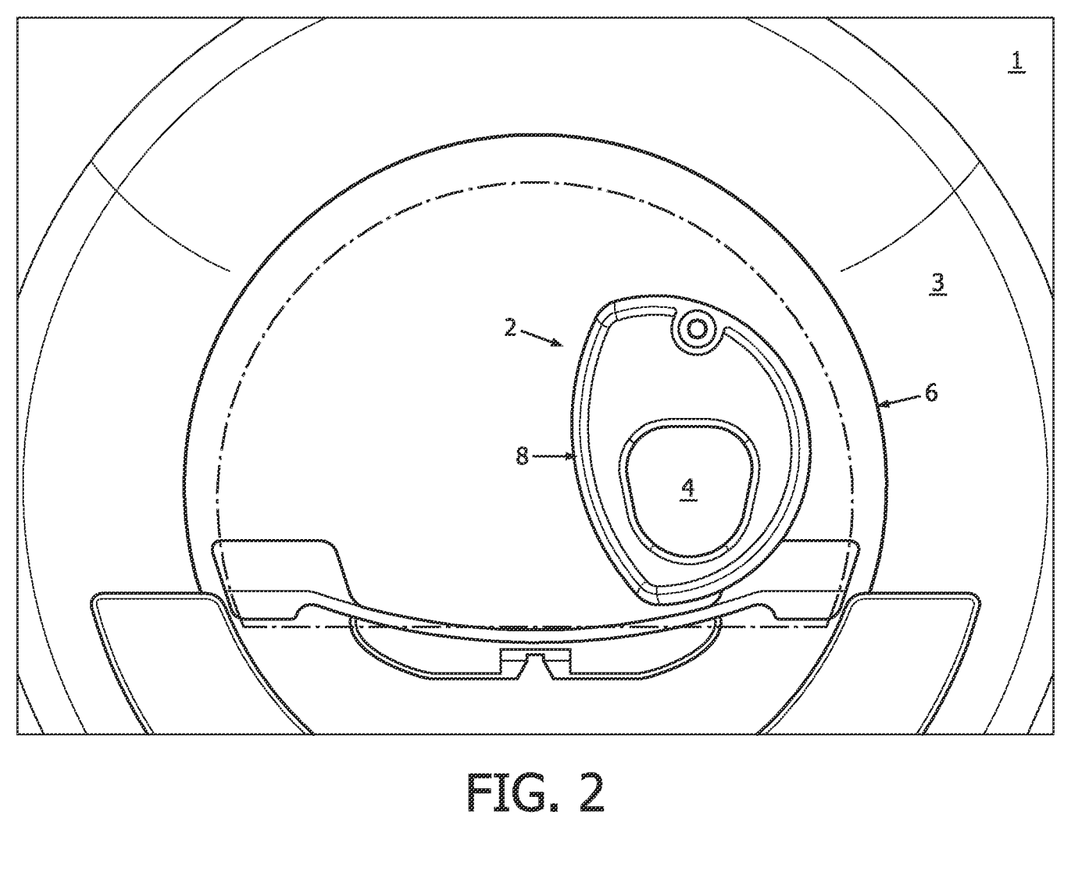
FIG. 2 shows a perspective view of an MRI apparatus with an inner coil housing with a transverse bore in which a portion of a patient's anatomy is to be positioned.
Figure 3:
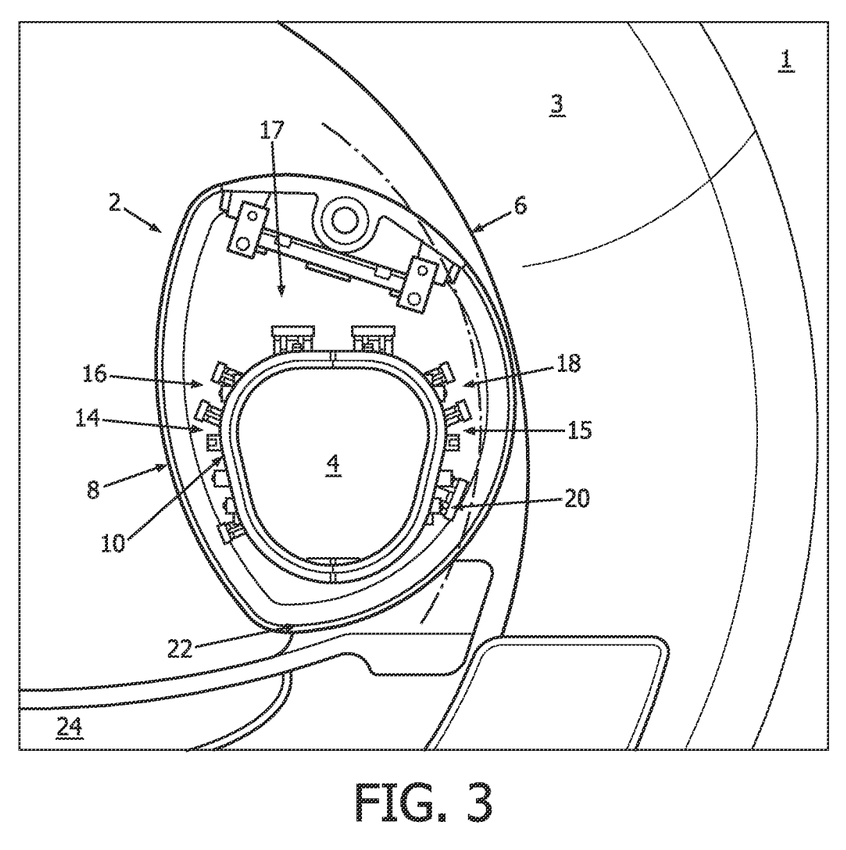
FIG. 3 shows a cross-sectional view of the inner coil housing with and its electronic components.

The MR apparatus 1 illustrated in FIGS. 1-3 in accordance with emplary embodiments can include a coil housing 2 with electronic coil components surrounding a transverse anatomy receiving space 4.

As illustrated in FIG. 1, the coil housing 2 can be placed inside the bore of the MR apparatus, which is within the magnetic field generated by the main magnet 3. The housing of the main magnet forms a housing bore 5 with an inner diameter ($M_D$) of approximately 27 inches or, more specifically, 27.6 inches, in one exemplary MR apparatus. Those skilled in the art will understand that all the dimensions used in this application are illustrative only of an exemplary MR apparatus and that MR apparatus which differ from this exemplary apparatus in all or some of these dimensions may be accommodated by an exemplary coil housing so long as the geometry of the housing is selected as described below to obtain the desired positioning of the anatomy receiving space within the coil housing and of the electronic components within the coil housing relative to the main magnet of the MR apparatus. Thus, as would be understood by those skilled in the art, the various dimensions given are merely illustrative of one possible coil housing designed for use with this MR apparatus and that modifications to any or all of the dimensions of the coil housing may be made as necessary to design a coil housing for use with any of a wide range of MR apparatus. Within this housing bore 5, an imaging area is formed (i.e., an area within which objects may be successfully imaged). In an exemplary embodiment, this imaging area can have a diameter ($I_D$) of approximately 23 inches or, more specifically, 23.6 inches in the example MR apparatus. Concentrically within this imaging area, a homogenous imaging area is typically formed with a diameter of 48 cm (18.9 inches) when measured to a homogenous factor of 10 parts per million. In the MR apparatus 1 according to an embodiment, the homogeneous imaging area can have, for example, a diameter ($H_D$) of approximately 17 inches or, more specifically, 17.7 inches in the example MR apparatus. The housing bore 5 also defines a restricted area (R) which is an area surrounding the inner diameter of the housing bore 3 in which the magnetic field may be strong enough to interfere with the proper functioning of various electronic components. Thus, the coil housing 2 includes a spacer shaped so that electronic components in the coil housing 2 are preferably not inside the restricted area (R) whenever the coil housing 2 is in an operative position within the housing bore 3. Specifically, in this example, electronic components such as the magnetic coils located in the coil housing 2 will preferably be at least 0.8 inches from the housing bore wall and preferably will be placed no closer than 0.4 inches from the housing bore wall to ensure their proper functioning. The lateralmost antenna loop, not including any electronic components—e.g., capacitors or preamps—should remain a distance C in FIG. 1 of at least 10.5 cm (4") from the bore wall 6 of the housing bore 5. Furthermore, as will be described in more detail below, the spacer of the coil housing 2 is also shaped so that a target portion of the patient's anatomy (i.e., the portion to be imaged) is maintained within the imaging area.

As would be understood by those skilled in the art, the coil housing 2 may be shaped to facilitate its insertion into the housing bore 5 by, for example, rounding the leading edges at which the coil housing 2 will initially contact the MR apparatus 1 and/or by treating the surface to reduce friction between the coil housing 2 and the bore wall 6 of the housing bore 5. For example, surfaces which may contact the bore wall 6 may be treated/coated with a low-friction material. As illustrated in FIG. 2, the shape of the coil housing 2 is generally dictated by the electronic coil elements contained therein, as well by the size and shape of the internal space receiving the target portion of the patient's anatomy. The coil housing 2 is generally formed as an asymmetric, vaguely toroidal element with electronic components including coil elements positioned around an anatomy receiving space 4. As would be understood by those skilled in the art, the anatomy receiving space 4 of an exemplary coil housing 2 forms a lumen extending through the entire housing and open to an exterior of the housing at both ends. Electronic components are arranged in a space radially outside this anatomy receiving space 4 and radially within an outer wall 8 of the coil housing 2. As would be understood by those skilled in the art, the coil housing 2 is preferably sized to minimize its size radially (i.e., in directions perpendicular to a longitudinal axis of the anatomy receiving space 4) to leave as much of the space within the housing bore 5 available to the patient as is possible.

As illustrated in FIG. 3, a space 14 within an interior side 16 of the coil housing 2 (i.e., a side of the housing 2 which, in use, faces the patient) is thin. This space 14 between the inner wall 10 and the outer wall 8 is preferably only as thick as necessary to accommodate any electronic components such as the pre-amps 20 housed in the space 14. This minimizes the intrusion of the coil housing 2 into the space available to be occupied by the patient. As those skilled in the art will understand, the portion of the coil housing 2 adjoining the space 14 on the interior side 16 may be rested against the patient to stabilize the coil housing 2 during imaging. A space 15 within the exterior side 18 of the coil housing 2 (i.e., the side of the coil housing 2 which, in use, faces the nearest surface of the bore wall 6) is thicker than the space 14 on the interior side 16 of the coil housing 2 to form a spacer which maintains the position of the coil housing 2 within the bore of the MRI apparatus in a desired position to achieve the desired positioning of target anatomy as well as internal components of the coil housing 2. That is, in this embodiment, the spacer is formed by a portion of the outer wall 8 on the exterior side 18 which curves away from the inner wall 10 so that the space between the inner wall 10 and the outer wall 8 on the exterior side 18 is greater than a distance between the inner wall 10 and the outer wall 8 on the interior side 16 of the coil housing 2. On the exterior side 18 of the coil housing 2, the outer wall 8 may extend radially outward from the inner wall 10 by a distance greater than that required to accommodate the components to he housed therein. This spacer—i.e., the increased radial separation between the inner wall 10 and the outer wall 8, is sized to maintain a target portion of the patient's anatomy within the anatomy receiving space 4 within the imaging area of the device—i.e., contact between the coil housing 2 and the bore wall 6 prevents the anatomy receiving space 4 from being moved radially outward toward the main magnet 3 beyond the diameter $I_D$.

For example, in this exemplary coil housing 2, the spacer maintains a minimum distance between the closest portion of the anatomy receiving space 4 and the wall 8 on the exterior side 18 of the coil housing 2 of approximately 5 inches or, more particularly, approximately 5.3 inches while maintaining a between the surface of the inner wall 10 and the exterior side 18 of the outer housing wall 8 of approximately 1 inch or, more particularly, 1.3 inches. This exemplary coil housing 2 may have a height of approximately 12 inches or, more specifically, 12.25 inches, and a length along the anatomy receiving space 4 of approximately 8 inches or, more specifically, 8.6 inches. The height of this exemplary coil housing 2 may be approximately 12 inches or, more specifically, 12.3 inches. Those skilled in the art will understand that a radius of curvature of a central side of the outer wall 8 (i.e., the side which, in use, faces the patient) may be made greater than a radius of curvature of the exterior side 18 of the outer wall 8 (i.e., the side which, in use, faces the near bore wall 6 of the bore housing 5). This smaller radius of curvature ensures that the exterior side 18 of the outer wall 8 extends further radially outward from the inner wall 10 than does the interior side 16. This radius of curvature in this exemplary coil housing 2 may be approximately 6 inches or, more particularly, 6.2 inches.

Furthermore, size of the spacer, formed in this embodiment by the increased radial separation between the inner wall 10 and the outer wall 8 on the exterior side 18 is selected so that, no matter how close the coil housing 2 is placed to the wall 6 of the housing bore 5, selected components located in the coil housing 2 are prevented from moving into a restricted area adjacent to the housing bore 5. The distance between the closest electronic component 20 to the bore wall 6 is determined, so that the electronic components stay at least a desired distance from the bore wall 6. In an exemplary embodiment, this distance is between 1.3 inches and 1.4 inches. The base 22 of the coil housing 2 is shaped so that it may rest stably on the patient table 24 against the bore wall 6 without requiring any extra supportive devices. In an example, the base 22 may come to a point to ensure that the coil housing 2 does not shift toward the patient's body. Those skilled in the art will understand that any other suitable arrangement may be employed to prevent the coil housing 2 from undesired shifting toward the patient.

As illustrated in FIG. 3, the transverse anatomy receiving space 4 extends longitudinally through the coil housing 2 so that the electronic coil elements 20 are situated between the anatomy receiving space 4 and the outer housing wall 8. The anatomy receiving space 4 can have a generally deltoid design with rounded corners, similar to known devices, with the width of the anatomy receiving space 4 decreasing toward the bottom of the anatomy receiving space 4. This deltoid design allows better coil to tissue contact as would be understood by those skilled in the art.

Figure 4:
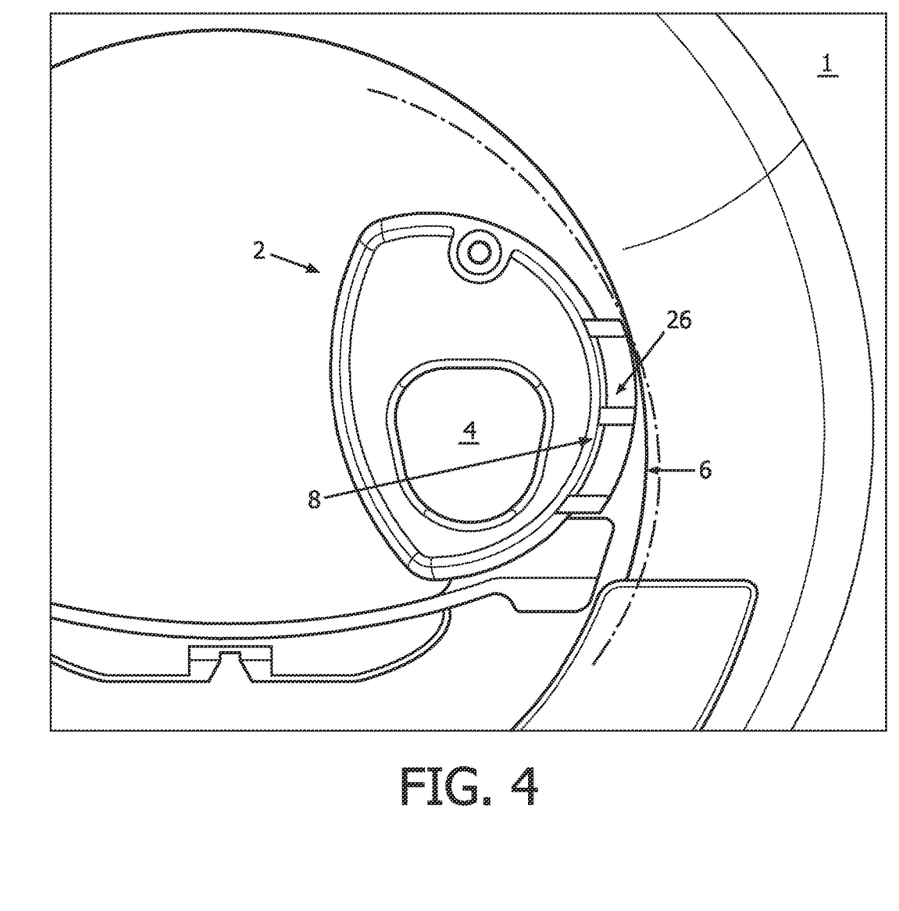
FIG. 4 shows an enlarged view of the inner coil housing with an example extrusion part attached to the external housing wall.
Figure 5:
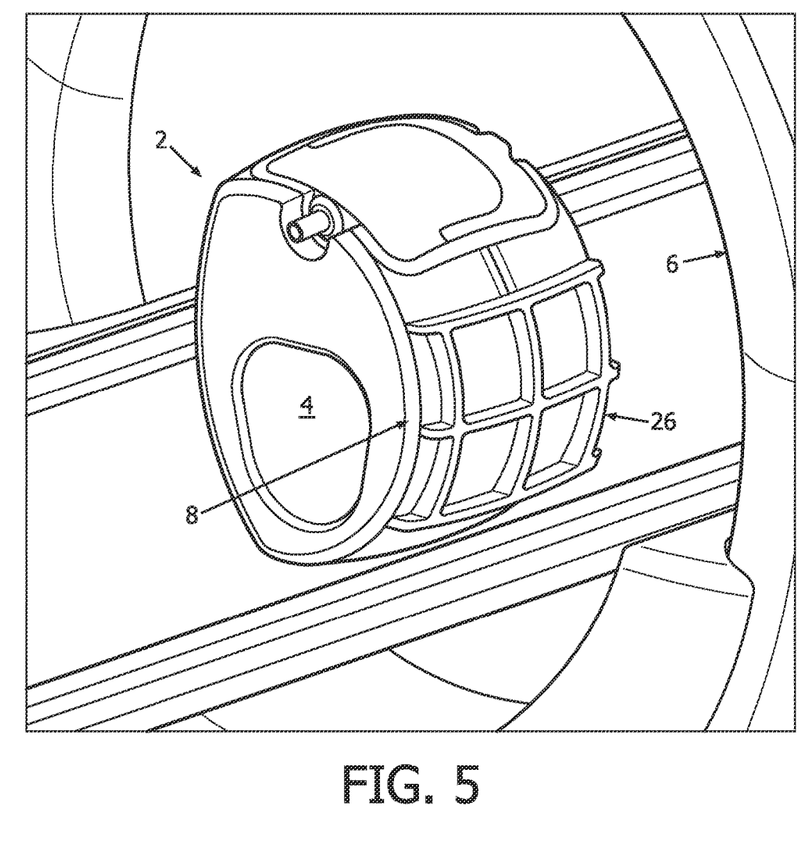
FIG. 5 shows a lateral view of the inner coil housing with an example extrusion part attached to the external housing wall.

As illustrated in FIGS. 4 and 5, a spacer for a coil housing 2' according to a further embodiment may optionally include a separately attached extender 26. This extender 26 may be permanently fixed to the lateral side of the outer housing wall 8 or it may be removable. As would be understood by those skilled in the art, the extender 26 may be coupled to the exterior side of a housing 2' which is otherwise symmetrical so that the extender 26 forms the entire spacer and itself is shaped to provide the entire differential in shape between the interior side 16 and the exterior side 18. Alternatively, the extender 26 may be used in conjunction with an asymmetric coil housing such as the coil housing 2 of FIG. 1 to achieve a different asymmetry to, for example, supplement the increased space within the coil housing 2 on the exterior side 18 as desired.

The extrusion part 26 may, for example, include a quick snap attachment. The extender 26 may be used as a distance modifier to increase the clearance between the anatomy receiving space 4 and the housing bore 5. For example, for a smaller patient where there is more space available closer to the center of the housing bore 5, it may be desirable to move the coil housing 2 further toward the center until, the entire anatomy receiving space is in the homogeneous imaging area (i.e., within $H_D$). In this case, the extender 26 may be attached so that the coil housing 2 cannot be moved radially outward to position the anatomy receiving space outside the homogeneous imaging area. As would be understood by those skilled in the art, the extender 26 may have different thicknesses for different sized patients or to accommodate different portions of the anatomy. Alternatively, the thickness of the extender 26 may be mechanically adjustable using any known mechanisms as would be understood by those skilled in the art. The extender 26 may also have lead in features and low-friction surface treatment to facilitate the sliding of the coil housing 2 into the housing bore 5 along the bore wall 6.

It is noted that the claims may include reference signs/numerals in accordance with PCT Rule 6.2(b). However, the present claims should not be considered to be limited to the exemplary embodiments corresponding to the reference signs/numerals.

The exemplary embodiments have been described with reference to specific exemplary embodiments. Those skilled in the art will understand that changes may be made in details, particularly in matters of size, shape, materials and arrangements of parts. The specification and drawings are, therefore, to be regarded in an illustrative rather than a restrictive sense.

What is claimed is:

1. A coil housing for a magnetic resonance ("MR") imaging apparatus, comprising:
    an anatomy receiving space defined by the coil housing, shaped and sized to receive at least a portion of a patient's anatomy to be imaged;
    a spacer shaped to maintain the anatomy receiving space a first distance from a bore wall of the MR imaging apparatus, the first distance defining an imaging area of the MR imaging apparatus, and
    an outer wall and an inner wall with an interior space between the outer wall and inner wall, the outer wall defining a central side which, when the housing is in use, faces a center of a bore of the MR imaging apparatus and a lateral side which, when the housing is in use, faces the bore wall of the MR imaging apparatus, the spacer being formed by a portion of the lateral side of the outer wall shaped to expand, by a first distance, a spacing between the inner wall and the portion of the lateral side of the outer wall relative to a space between the inner wall and the central side of the outer wall; and
    wherein the anatomy receiving space is substantially deltoid in shape and where a radius of curvature of the central side of the outer wall is larger than a radius of curvature of the lateral side of the outer wall.

2. The coil housing according to claim 1 the housing includes a plurality of electronic components within the interior space distributed about at least a portion of a perimeter of the anatomy receiving space, wherein the spacer is shaped so that the spacing between the inner wall and the central side of the outer wall is selected to achieve a minimum desired clearance for electronic components to be housed therein and wherein the spacing between the inner wall and the lateral side of the outer wall is greater than a minimum clearance desired for the electronic components to be housed therein by a distance selected so that, when the lateral side contacts the bore wall, the electronic components in the interior space between the inner wall and the lateral side of the outer wall are at least a second distance from the bore wall, the second distance being less than the first distance.

3. The coil housing of claim 2, wherein the electronic components include magnetic resonance coils and wherein the spacer prevents the coils from being positioned less than 1.3 inches from the bore wall.

4. The coil housing of claim 2, wherein the electronic components include magnetic resonance coils and wherein the spacer prevents the coils from being positioned less than 1.4 inches from the bore wall.

5. The coil housing of claim 1, wherein the anatomy receiving space is formed as a lumen extending through the housing so that the housing may be rotated to place the lateral side of the outer wall on either a right or a left of an MR imaging apparatus.

6. The coil housing of claim 5, wherein a radius of curvature of the central side of the outer wall is between 10 inches and 10.5 inches and a radius of curvature of the lateral side of the outer wall is between 6 inches and 6.3 inches.

7. The coil housing of claim 1, wherein the spacer further comprises an extender coupled to the lateral side of the outer wall, the extender increasing by a desired distance a separation between the anatomy receiving space and the bore wall.

8. The coil housing of claim 7, wherein the extender is sized to maintain the entire anatomy receiving space within a homogeneous imaging area of the main magnet.

9. The coil housing of claim 7, wherein the extender is removably mountable on the housing to alter a clearance between the anatomy receiving space and the bore wall.

10. The coil housing of claim 1, further comprising a base portion of the outer wall shaped to engage a bed of an MR imaging apparatus to stably mount the housing thereon.

11. The coil housing of claim 1, wherein the lateral side of the outer wall is treated to reduce friction between the outer wall and an inner wall of the bore wall.

12. The coil housing of claim 5, wherein a width of a lower portion of the anatomy receiving space is smaller than a width of an upper portion thereof.

13. The coil housing according to claim 1, wherein the spacer is formed as a portion of the outer wall which, on the lateral side of the coil housing, extends further from the inner wall than a maximum separation between a portion of the outer wall on the central side of the coil housing.

14. The coil housing according to claim 13, wherein a distance between the inner wall and the portion of the outer wall on the central side of the coil housing is selected to be a minimum necessary to accommodate therein components of the housing and a distance between the inner wall and the portion of the outer wall on the lateral side of the coil housing is extended beyond that necessary to accommodate the components of the coil housing.

15. The coil housing according to claim 1, wherein the spacer projects radially outward from the outer wall to increase a projection of the coil housing toward the lateral side thereof.

16. The coil housing according to claim 15, wherein the spacer is permanently mounted to the outer wall.

17. The coil housing according to claim 15, wherein the spacer is removably mounted to the outer wall.

* * * * *